(12) United States Patent
Russell et al.

(10) Patent No.: US 10,481,115 B2
(45) Date of Patent: Nov. 19, 2019

(54) CALORIMETER WITH DIFFUSION-BONDED BLOCK

(71) Applicant: Waters Technologies Corporation, Milford, MA (US)

(72) Inventors: Donald J. Russell, Orem, UT (US); David Serrell, Draper, UT (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 214 days.

(21) Appl. No.: 15/423,738

(22) Filed: Feb. 3, 2017

(65) Prior Publication Data
US 2017/0227480 A1 Aug. 10, 2017

Related U.S. Application Data

(60) Provisional application No. 62/291,707, filed on Feb. 5, 2016.

(51) Int. Cl.
*G01N 25/20* (2006.01)
*H01L 37/02* (2006.01)

(52) U.S. Cl.
CPC ............ *G01N 25/20* (2013.01); *H01L 37/02* (2013.01)

(58) Field of Classification Search
CPC ................................ G01N 25/20; H01L 37/02
USPC ......... 374/10, 11, 12, 13, 31, 32, 33, 34, 45, 374/36, 37, 38, 39, 40, 41, 42; 422/51
See application file for complete search history.

(56) References Cited

U.S. PATENT DOCUMENTS

| | | | |
|---|---|---|---|
| 2008/0080586 A1* | 4/2008 | Huetter | G01K 7/028 374/31 |
| 2014/0092935 A1* | 4/2014 | Lin | G01N 25/48 374/10 |
| 2018/0108593 A1* | 4/2018 | Terasaki | B23K 11/185 |

FOREIGN PATENT DOCUMENTS

| | | | | |
|---|---|---|---|---|
| WO | 2008024455 A2 | 2/2008 | | |
| WO | WO 2008024455 A2 * | 2/2008 | ............ | G01K 17/00 |
| WO | 2014153438 A1 | 9/2014 | | |
| WO | WO 2014153438 A1 * | 9/2014 | ............ | G01K 17/00 |

OTHER PUBLICATIONS

Combined Search and Examination Report in UK Patent Application No. GB1701696.5, dated May 30, 2017; 6 pages.
Examination Report in UK Patent Application No. GB1701696.5, dated Dec. 14, 2017; 4 pages.

(Continued)

*Primary Examiner* — Natalie Huls
*Assistant Examiner* — Janice M Soto
(74) *Attorney, Agent, or Firm* — Schmeiser, Olsen & Watts LLP

(57) ABSTRACT

A calorimeter with a heat sink that includes a diffusion-bonded block that has higher thermal conductivity laterally across the block than through the block. The diffusion-bonded block has multiple metallic layers that are diffusion-bonded together, with relatively higher thermal conductivity layers alternating with relatively lower thermal conductivity layers. The diffusion-bonded block may be used in differential scanning calorimeters, multi-cell differential scanning calorimeters, nano-differential scanning calorimeters and isothermal titration calorimeters, as well as other calorimeters that measure differential heat flow to and/or from a sample with respect to the heat flow to and/or from a reference.

21 Claims, 12 Drawing Sheets

(56) References Cited

OTHER PUBLICATIONS

Examination Report in UK Patent Application No. GB1701696.5, dated Feb. 19, 2018; 4 pages.
Examination Report under Section 18(3) for GB Application No. 1701696.5, dated Jun. 27, 2018.
Examination Report in U.K. Patent Application No. GB1701696.5 dated Aug. 31, 2018; 3 pages.
Microcalorimetry, brochure, TA Instruments, 2012, New Castle, DE, 62 pp.

* cited by examiner

CALORIMETER WITH DIFFUSION-BONDED BLOCK

This application claims priority to U.S. Provisional Application No. 62/291,707, filed Feb. 5, 2016, which is incorporated by reference herein in its entirety.

BACKGROUND

The present embodiments relate generally to calorimeters that may be used to characterize materials such as pharmaceuticals, biologicals, proteins, cellular organisms, food products, industrial chemicals and other materials.

Calorimeters are instruments that may be used to measure changes in the energy of a sample of a material by measuring the heat flow between the sample and its surroundings. Examples of calorimeters include differential scanning calorimeters (DSCs) that may be used to measure heat flows associated with heating or cooling a material, or with thermal transitions in materials, and isothermal titration calorimeters (ITCs) that may be used to measure heat as it is absorbed or released during a reaction between two chemicals. DSCs generally have at least one sample cell and at least one reference cell. In a typical DSC measurement, the temperature of the sample cell and of the reference cell is increased or decreased in a controlled manner, although some experiments or measurements may be done at a single temperature. In temperature ranges in which the sample does not undergo a transition, the heat capacity of the sample may be measured by measuring the differential heat flow needed to heat (or cool) the sample compared to the reference. Also, when the sample is heated or cooled through an exothermic or endothermic phase transition, for example, the differential heat flow to or from the sample compared to the heat flow to or from the reference may be used to calculate the enthalpy of the transition.

ITCs generally have a sample cell and a reference cell. ITCs may operate on the power compensation principle, in which the difference in the amount of power required to keep the sample cell and the reference cell at the same temperature is measured. This difference in power is a measure of the heat absorbed or released during a measurement. In a typical ITC measurement, the sample cell contains a first material. Small quantities of a second material are injected gradually and sequentially into the sample cell using, for example, a syringe. When the molecules of the second material react with or bind with the molecules of the first material, heat is either absorbed or released. The ITC's sensors detect the temperature difference between the sample cell and a reference cell due to the binding reaction, and provide feedback to the heaters for the sample and for the reference. The heaters then compensate for the difference between the sample cell and the reference cell, bringing the temperature of the sample cell equal to the temperature of the reference cell. The difference in the power applied to the sample compared to the power applied to the reference needed to achieve this compensation may be used as a measure of the heat absorbed or released during the measurement.

SUMMARY

The embodiments of the calorimeters disclosed herein generally include metal plates or blocks that provide the thermal connections between the sample cell or cells, the reference cell and the temperature sensing and controlling modules that are used to operate the calorimeter. Embodiments of calorimeters described below have one or more metal plates or blocks that, instead of being machined from a single metal, have multiple metallic layers that are diffusion-bonded together to produce a metallic block with the unique property of having a higher thermal conductivity laterally across the block than through the block, as described below. The multiple metallic layers may, for example, may be layers of a highly conductive metal (such as copper, silver, gold or aluminum) alternating with layers of a less conductive metal (such as stainless steel, Inconel, bronze, or titanium). The use of a multiple layer diffusion-bonded block reduces the noise level in the calorimeter, allows the calorimeter to reach equilibrium in a much shorter time and greatly reduces any deviation between the cells in the calorimeter.

In one embodiment, a calorimeter has a sample cell thermally coupled to a sample temperature sensor, a reference cell thermally coupled to a reference temperature sensor, and a common heat sink thermally coupled to the sample cell and to the reference cell. The common heat sink includes a diffusion-bonded block, which has at least three layers: a first metallic layer that has a first thermal conductivity, a second metallic layer that has a second thermal conductivity and a third metallic layer that has a third thermal conductivity. The diffusion-bonded block may have five, seven or more metallic layers. The thermal conductivities of the first, third and other odd-numbered layers are greater than the thermal conductivities of the second metallic layer and of any other even numbered layers.

In another embodiment, a calorimeter system has at least one sample cell and at least one reference cell in thermal communication with a diffusion-bonded block, and a temperature probe positioned to measure the temperature of the diffusion-bonded block. A computer is in electrical communication with the temperature probe and with either (a) a sample temperature sensor measuring a sample cell temperature and a reference temperature sensor measuring a reference cell temperature; or (b) a differential temperature sensor measuring a differential temperature between the sample cell and the reference cell. The computer has a temperature control algorithm and a feedback control algorithm that control the temperature of the sample cell and the temperature of the reference cell; and calculates the differential heat flow to the sample cell with respect to the reference cell.

In yet another embodiment, a calorimeter has a sample cell and a reference cell, and a diffusion-bonded block thermally coupled to the sample cell and to the reference cell. The diffusion-bonded block has a first metallic layer diffusion-bonded to a second metallic layer, a third metallic layer diffusion-bonded to the second metallic layer and to a fourth metallic layer, and a fifth metallic layer diffusion-bonded to the fourth metallic layer. The first metallic layer, the third metallic layer and the fifth metallic layer are characterized by having relatively higher thermal conductivities and the second metallic layer and the fourth metallic layer are characterized by having relatively lower thermal conductivities. The first metallic layer incorporates a temperature probe for measuring the temperature of the diffusion-bonded block.

Other systems, methods, features and advantages of the embodiments will be, or will become, apparent to one of ordinary skill in the art upon examination of the following figures and detailed description. It is intended that all such additional systems, methods, features and advantages be included within this description and this summary, be within the scope of the embodiments, and be protected by the following claims.

BRIEF DESCRIPTION OF THE DRAWINGS

The embodiments can be better understood with reference to the following drawings and description. The components in the figures are not necessarily to scale, emphasis instead being placed upon illustrating the principles of the embodiments. Specifically, while the drawings in this patent specification are presented for the purpose of describing embodiments of the diffusion-bonded block schematically, the dimensions shown in the figures should not be understood and are not intended to convey the actual dimensions or relative proportions of the various components of the diffusion-bonded block. Finally, in the figures, like reference numerals designate corresponding parts throughout the different views.

DETAILED DESCRIPTION

The disclosure herein of embodiments of calorimeters with diffusion-bonded blocks should not be limited to the particular embodiments described herein. Instead, the disclosure may be applied to any calorimeter comprising one or more diffusion bonded blocks as well as other features described herein and recited in the claims.

Calorimeters, including DSCs, ITCs and other calorimeters, generally include metal plates or blocks that provide the thermal connections between the sample cell or cells, the reference cell and the temperature sensing and controlling modules that are used to operate the calorimeter. Embodiments of calorimeters described below have one or more metal plates or blocks that, instead of being machined from a single metal, have multiple metallic layers that are diffusion-bonded together to produce a metallic block with the unique property of having a higher thermal conductivity laterally across the block than through the block, as described below. The multiple metallic layers may, for example, have layers of a highly conductive metal (such as copper, silver, gold or aluminum) alternating with layers of a less conductive metal (such as stainless steel, Inconel, bronze, or titanium).

For example, embodiments of the diffusion-bonded block may have a first layer of copper, a second layer of stainless steel, a third layer of copper, a fourth layer of stainless steel and a fifth layer of copper. Other embodiments may have for example, three layers of copper, stainless steel, and copper; seven layers of copper, stainless steel, copper, stainless steel, copper, steel and copper; or nine layers of copper, stainless steel, copper, stainless steel, copper, stainless steel, copper, steel and copper. Yet other embodiments may have, for example, sequential layers of silver, stainless steel, silver, stainless steel and silver; or copper, stainless steel, silver, stainless steel and copper, for example. Yet other embodiments may use aluminum or gold layers instead of copper layers, or Inconel, bronze or titanium layers instead of the stainless steel layers. In some embodiments, the thermal conductivity of the higher conductivity layers (e.g., the first layer, the third layer and the fifth layer) is at least five times greater than the thermal conductivity of the lower conductivity layers (e.g., the second layer and the fourth layer).

Figure 1A:
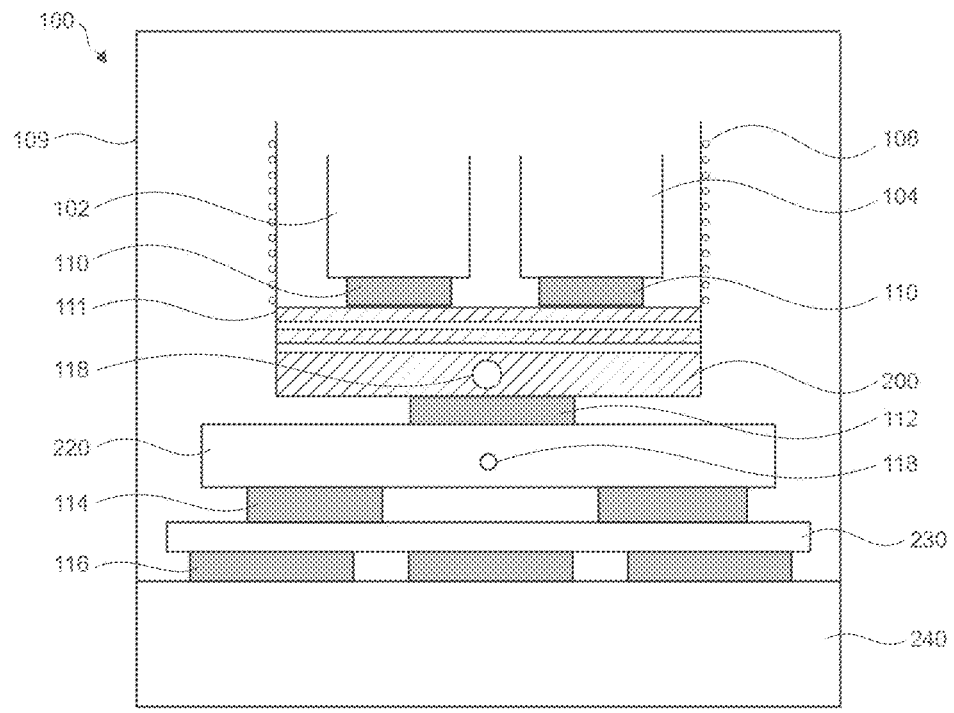
FIG. 1A is a schematic diagram of an embodiment of a multi-cell differential scanning calorimeter.

FIG. 1A is a schematic diagram of a cross-section of an embodiment of a multi-cell differential scanning calorimeter (MCDSC) 100 that may use one, two or three diffusion-bonded blocks to provide the thermal connections between the sample and reference cells and the temperature sensing and controlling elements of the calorimeter. In this embodiment, the MCDSC is a heat flux DSC, although in other embodiments, it may be a power compensation DSC.

Figure 1B:
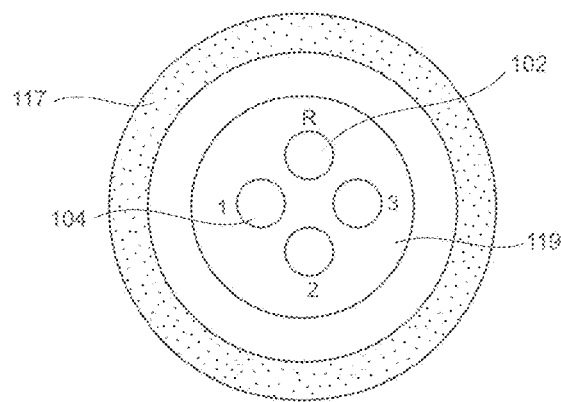
FIG. 1B is a schematic diagram showing a plan view of the cell compartment of the multi-cell DSC shown in FIG. 1A.

As shown in the cross-section of FIG. 1A and the plan view of the cell compartment 119 shown in FIG. 1B, the MCDSC 100 has one reference cell 102 and three sample cells 104 mounted symmetrically around the center of an adiabatic shield 111 mounted within a heated jacket 108. A cover (not shown) may fit over gasket 117 to close compartment 119. These components are enclosed within a housing 109 which allows the atmosphere within the MCDSC to be controlled, for example by introducing dry nitrogen into the housing. The reference cell and the sample cells are shown in FIG. 1B, which is a top view of the compartment 119 holding the three sample cells 104 and the reference cell 102. The reference cell and each of the sample cells are each mounted on a thermoelectric device (TED) 110 (which may also be referred to as a Peltier module), that functions as a temperature sensor. Thus there are four TEDs or Peltier modules, one mounted below the reference cell, and one each mounted below each of the three sample cells. These TEDs in turn are mounted on a common heat sink. The temperature of this heat sink is monitored using, for example, a platinum resistance temperature detector (RTD) 118.

The exemplary embodiment of an MCDSC shown schematically in FIG. 1A may be operated using continuous temperature-scanning, step-scanning or isothermally to identify phase transitions, metabolic activity in cellular organisms or thermal events occurring in liquids or solids during admixing.

In the embodiment shown in FIG. 1, the heat sink is a diffusion-bonded block 200 (which is described below with reference to FIGS. 2-5). Diffusion-bonded block 200 is mounted on a scanning TED 112, which may be used to scan the temperature of the calorimeter through a temperature range.

Scanning TED 112 is mounted on a second block 220. The temperature of block 220 may be monitored by a temperature sensing probe 118, which may be, for example, an RTD. In some embodiments, block 220 may be a diffusion-bonded block. In other embodiments, block 220 may be a solid copper, silver, gold or aluminum block, for example. Block 220 is mounted on following TEDs 114, which are mounted on a third block, 230. Block 230 may be a diffusion-bonded block. In other embodiments, block 230 may be a solid copper, silver, gold or aluminum block, for example, or may be another conductive block. Block 230 may be mounted on an additional set of following TEDs 116, which are mounted over a water bath 240. Alternatively, block 230 may be mounted directly onto water bath 240. Following TEDs 116 may be used to cool the reference cell and the scan cells to a temperature below the temperature of the water bath, for example to a temperature 30° C. below the temperature of the water bath, or may also be used to heat the reference and sample cells to a temperature above the temperature of the water bath. In order to further raise the temperature of the MCDSC, heater jacket 108 may be used to raise the temperature of the reference cell and the sample cells to an elevated temperature, such as 200° C.

Figure 6:
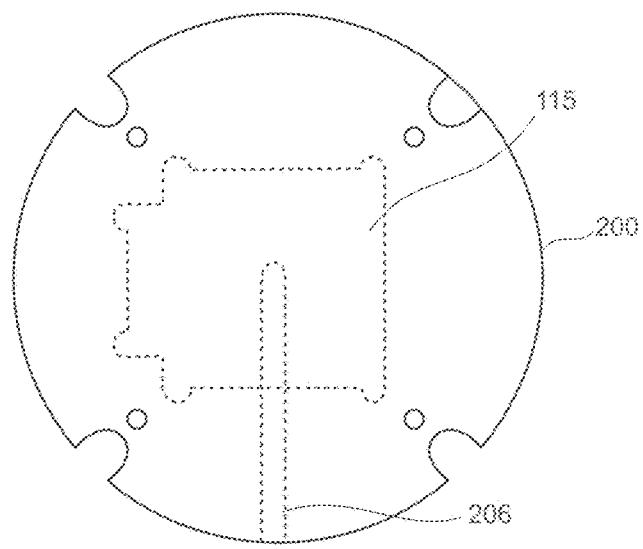
FIG. 6 is a top view of the diffusion-bonded block assembly of FIG. 5.
Figure 7:
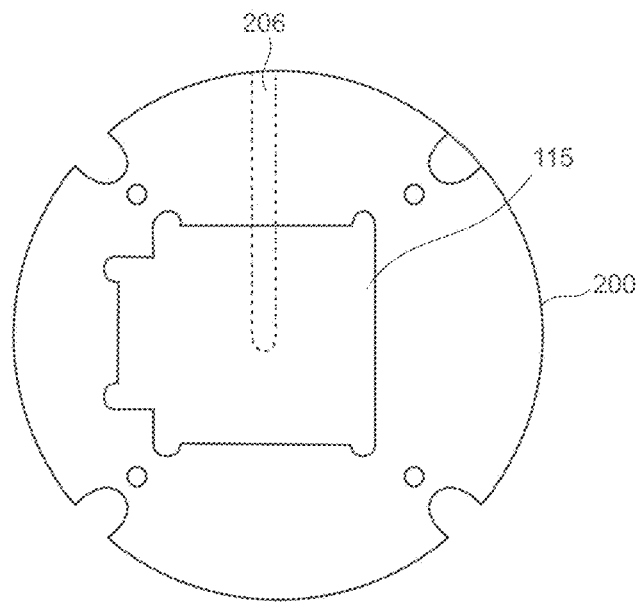
FIG. 7 is a bottom view of the diffusion-bonded block assembly of FIG. 5.

Diffusion-bonded block 200 includes a temperature sensing probe 118, as shown below in FIGS. 6 and 7. Temperature sensing probe 118 extends from the periphery of diffusion-bonded block 200 to the center of diffusion-bonded block 200. Temperature sensing probe 118 may be, for example, a resistance temperature detector (RTD), such as a platinum RTD. Block 220 also includes a temperature sensing probe 118, which may also be a platinum RTD.

In operation, one, two or three sample cells and one reference cell are placed into the MCDSC, as described below with respect to FIG. 1A. A temperature range may be selected for an experiment or a measurement. If necessary, the MCDSC may be brought to a temperature below this temperature range using following TEDs 114 and/or using heater jacket 108. The temperature of the sample and reference cells is then scanned through the selected temperature range by scanning TED 112. Sensing TEDs 110 are used to calculate the differential heat flow between to or from each of the sample cells with respect to the reference cell.

Figure 2:
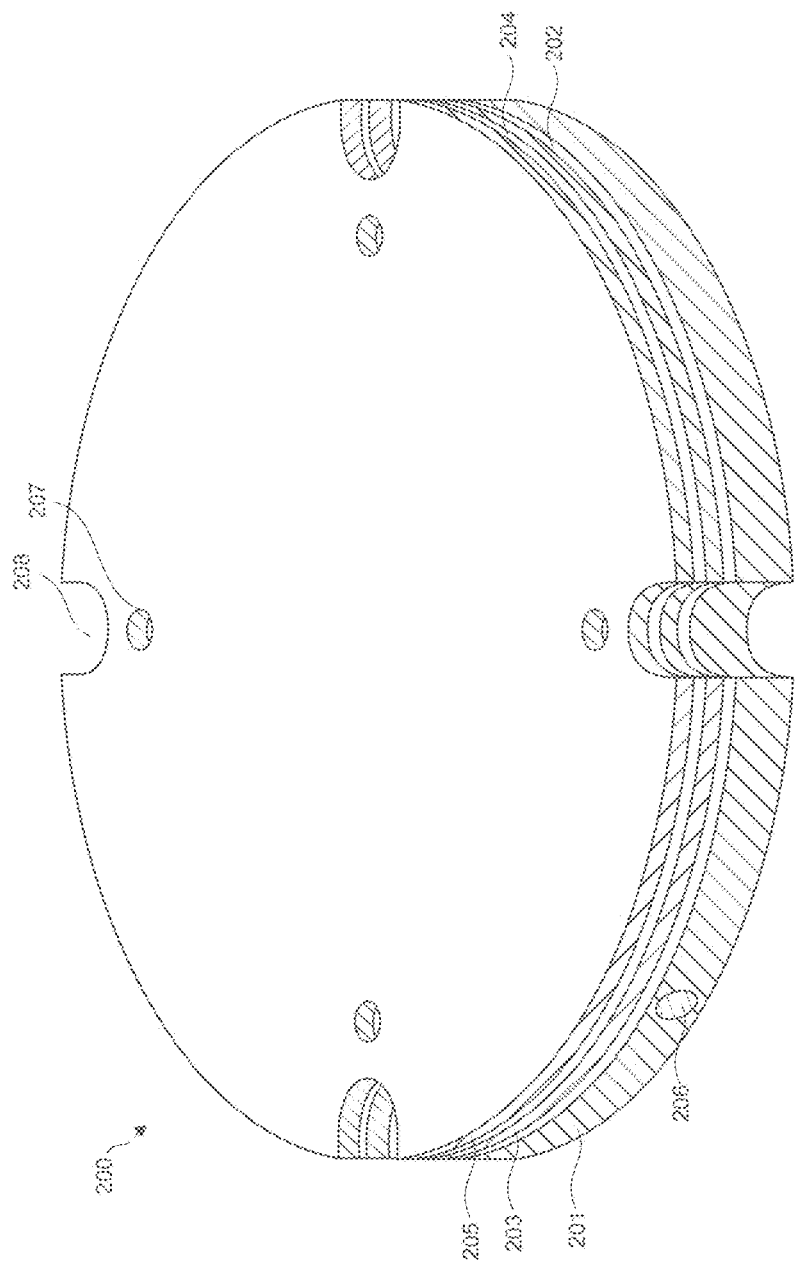
FIG. 2 is a schematic diagram of a five-layer diffusion-bonded block.
Figure 3:
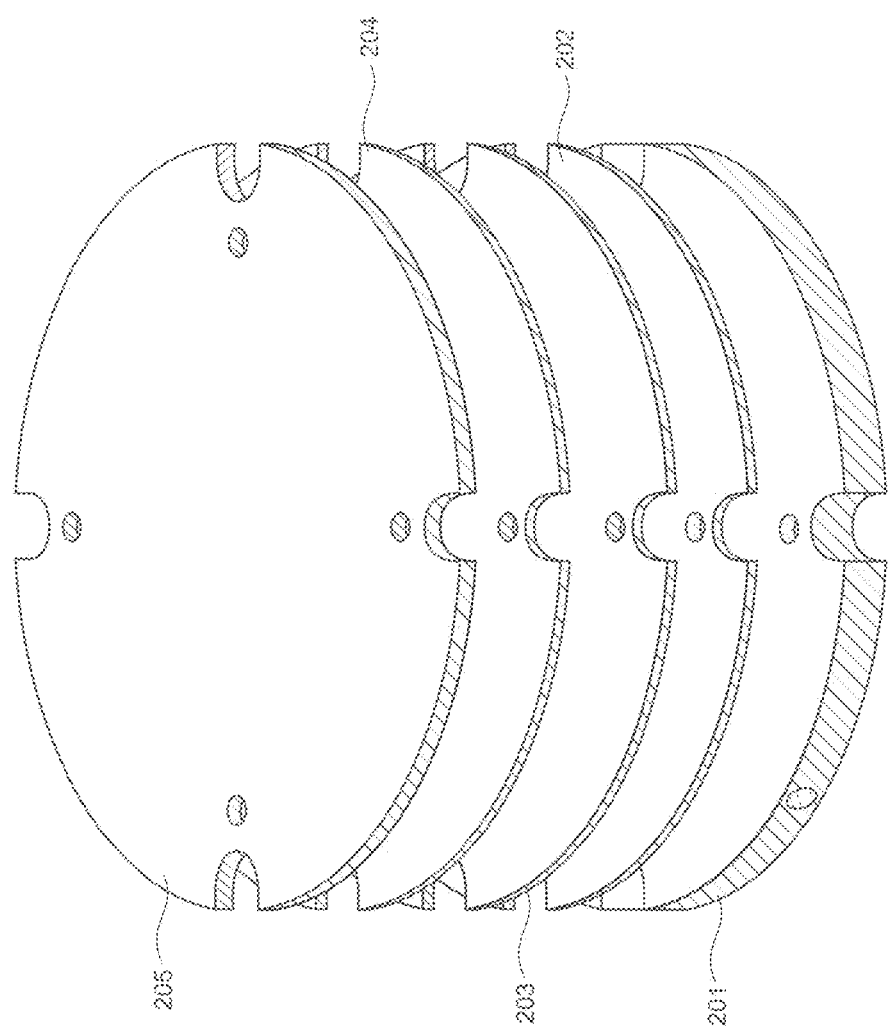
FIG. 3 is an exploded view of the five-layer diffusion-bonded block of FIG. 2
Figure 4:
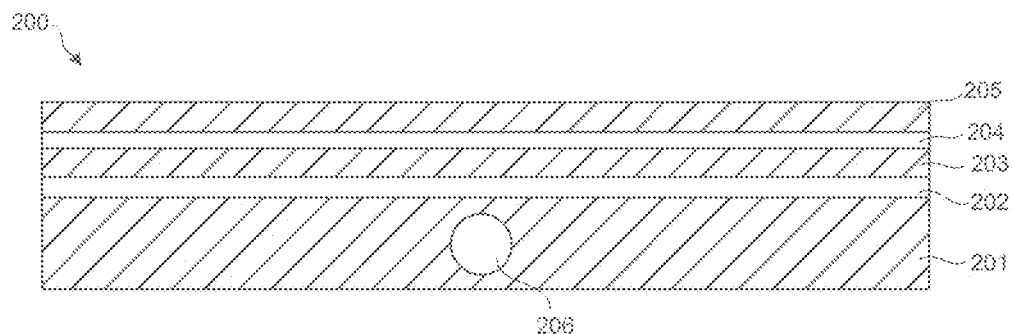
FIG. 4 is a schematic diagram of an elevation view of the five-layer diffusion-bonded block of FIG. 2.

FIGS. 2-4 illustrate diffusion-bonded block 200. In this embodiment, diffusion-bonded block 200 has five metallic layers: a first copper layer 201, a first stainless steel layer 202, a second copper layer 203, a second stainless steel layer 204 and a third copper layer 205. Layer 201 has sufficient thickness to incorporate a tubular opening 206 (into which a temperature sensing probe such as probe 118 may be inserted). For example, layer 201 may be in the range of approximately 0.150-0.200 inches thick, such as approximately 0.187 inches thick. Stainless steel layers 202 and 204 may be, for example, approximately 0.025 to 0.050 inches thick, such as approximately 0.036 inches thick. Copper layers 203 and 205 may be, for example, approximately 0.050 to 0.080 inches thick, for example, approximately 0.062 inches thick.

Holes 207 in diffusion-bonded block 200 may be, for example, used to hold the stack of copper layer 201, stainless steel layer 202, copper layer 203, stainless steel layer 204 and copper layer 205 together prior to diffusion-bonding these layers to form diffusion-bonded block 200. Recesses 208 hold diffusion block 200 within adiabatic shield 111.

Figure 5:
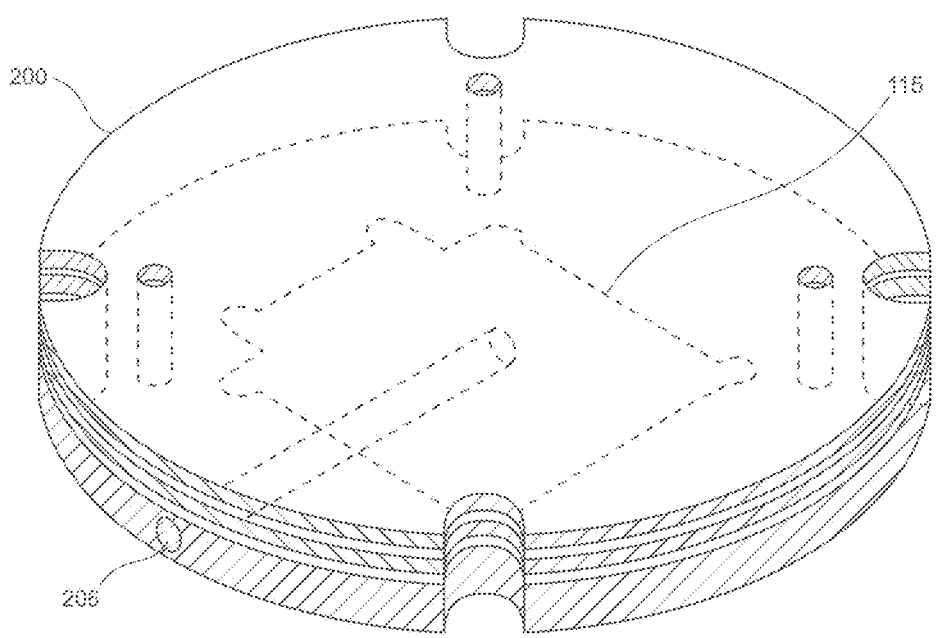
FIG. 5 is a perspective view of an embodiment of a diffusion bonded block assembly.

FIG. 3 is an exploded view of diffusion-bonded block 200, showing each of copper layer 201, stainless steel layer 202, copper layer 203, stainless steel layer 204 and copper layer 205 prior to diffusion bonding. FIG. 4 is an elevation view of the diffusion-bonded block 200, showing each of layers 201, 202, 203, 204 and 205, and also showing tubular opening 206. FIG. 5 is a perspective view of the diffusion-bonded block 200, with a recess 115 dimensioned to receive a scanning TED 112 in its bottom side. FIG. 6 and FIG. 7 are schematic top and bottom views, respectively, of diffusion-bonded block 200 showing recess 115 in the bottom of diffusion-bonded block 200. FIGS. 5-7 also show tubular opening 206, which is dimensioned to receive a temperature probe 118 such as an RTD (shown in FIG. 1), a thermocouple, or other temperature sensor.

Figure 8:
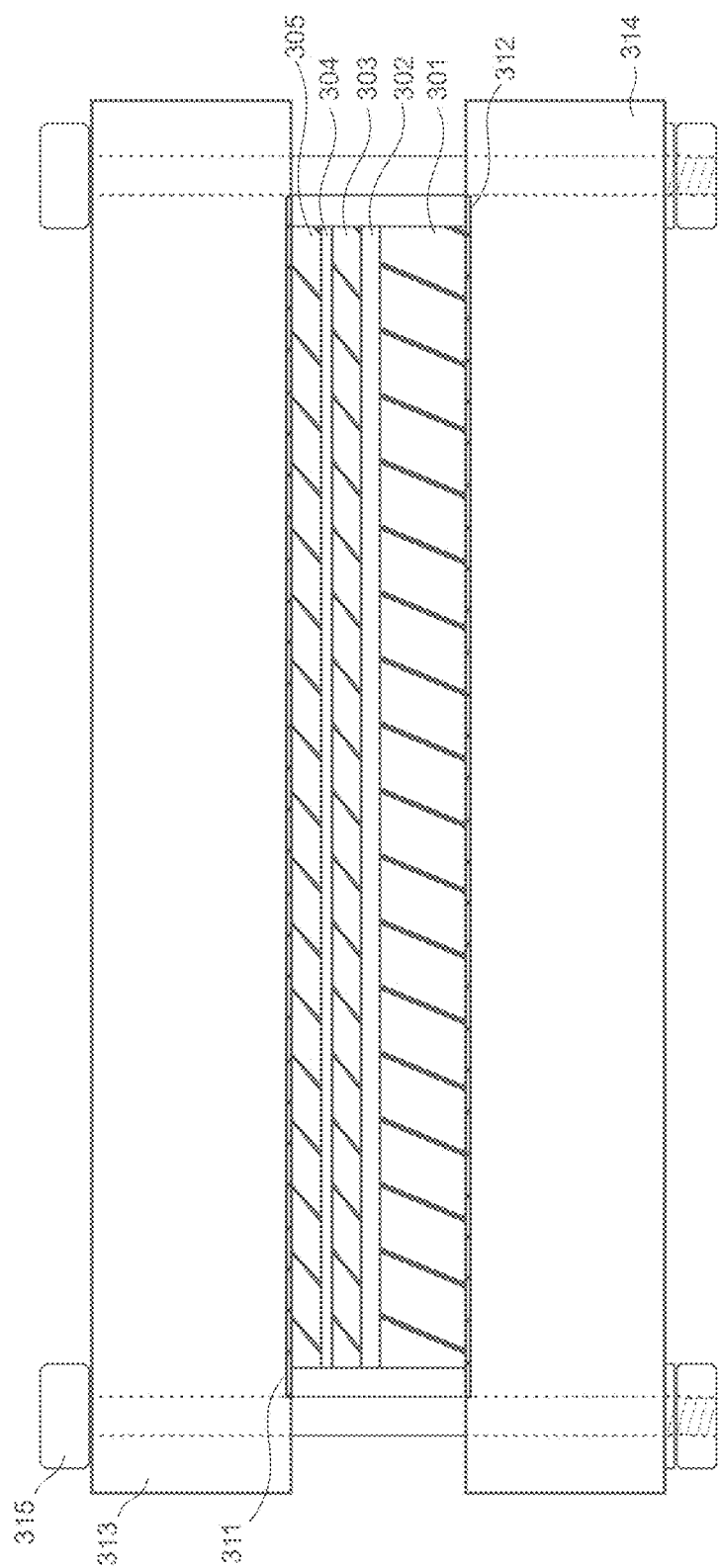
FIG. 8 is a schematic diagram of a fixture that may be used to manufacture the diffusion-bonded block of FIG. 2.

FIG. 8 is a schematic diagram of a fixture that may be used to manufacture an exemplary diffusion-bonded block. In this example, the first metallic layer 301 that is being bonded is a copper layer; the second metallic layer is a stainless steel layer 302; the third metallic layer is a copper layer 303; the fourth metallic layer is a stainless steel layer 304; and the fifth metallic layer is a copper layer 305. In this example, the stainless steel layer is a stainless steel layer (such as 316 stainless streel) that contains chromium, nickel and molybdenum. These five metallic layers are held between two relatively thick stainless steel plates 313 and 314. For example, in an exemplary implementation, the stainless steel plates may each be 0.5" thick, whereas the first metallic layer may be 0.187" thick, the second and fourth metallic layers may be 0.036" thick and the third and fifth metallic layers may be 0.062" thick. Other dimensions may also be used, as long as the overall structure has sufficient stability in its intended range of temperatures. The assembly is bolted together by, for example, four ½"-13 Mo bolts 315.

A thin layer of ceramic brazing stop-off paint 311 is applied to the face of stainless steel plate 313 that is in contact with copper layer 305 and a thin layer of ceramic brazing stop-off paint 312 is applied to the face of stainless steel plate 314 that is in contact with copper layer 301.

Diffusion bonding of the layers is achieved by placing the fixture in a furnace under a vacuum at an elevated temperature for an extended time period. For example, the fixture may be placed in a vacuum of $10^{-5}$ torr or better. The fixture may be held at a temperature in the range of 650° C. to 800° C. for a period of 2 to 10 hours, for example. A typical process might be, for example, holding the fixture at a temperature of 700° C. for a period of four hours. Higher temperatures would require shorter periods at the elevated temperatures, and lower temperatures would require longer periods at the elevated temperatures. Because the coefficient of expansion of the molybdenum bolts 315 is substantially lower than the coefficient of expansion of the stainless steel plates 313 and 314, the layers of copper and stainless steel are held together under an elevated stress as the temperature of the fixture is raised from room temperature to the diffusion bonding temperature. During the heat treatment, copper diffuses into the stainless steel layers and iron, chromium, nickel and possibly other constituents of the stainless steel layers diffuse into the copper layers, thus diffusion-bonding layers 301, 302, 303, 304 and 305 together. Ceramic brazing stop-off paint layers 311 and 312 prevent any diffusion-bonding between stainless steel plate 313 and copper layer 305, or between stainless steel plate 314 and copper layer 301.

In order to maximize the diffusion between the copper layers and the stainless steel layers, and to minimize any interface resistance to heat flow across a copper/stainless steel boundary, the surface finish of the facing surfaces of the copper layers and the stainless steel layers may be machined to be a smooth as possible. "Facing surfaces" in this context means the surfaces of the copper layer that are facing and are in contact with the stainless steel layers and the surfaces of the stainless steel layers that are facing and in contact with the copper layers.

For example, the surface finish of the surfaces of the layers that are to be diffusion-bonded may be machined prior to placing them in the diffusion-bonded fixture so that they have a surface roughness of 4-8 micro-inches or less. In addition, in order to minimize discrepancies between the heat flow to or from the different cells, the top surface of the top layer of the diffusion-bonded block may be parallel to the bottom surface of the diffusion-bonded block to within 0.002" or less. The surface roughness of the top surface and of the bottom surface of the diffusion-bonded block may be 0.032" or less.

Figure 9:
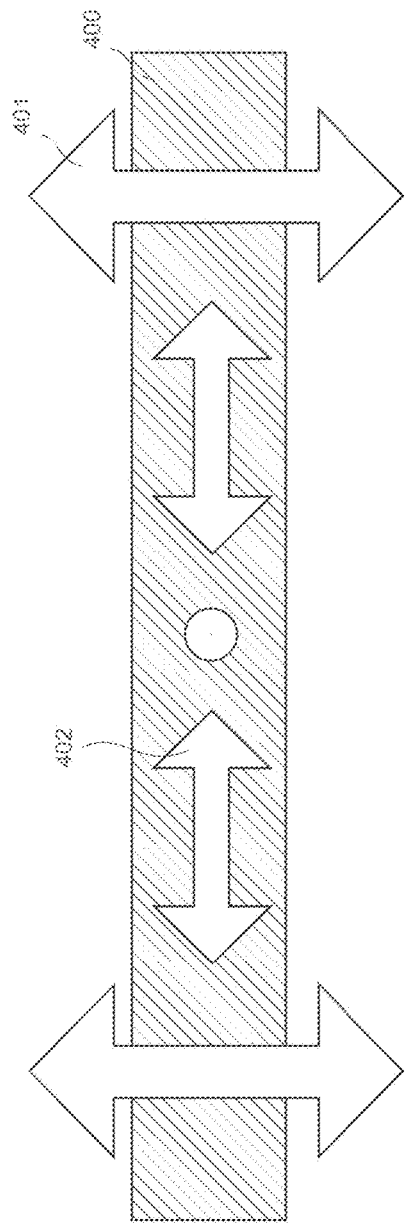
FIG. 9 is a schematic diagram illustrating heat flow in a solid copper block.
Figure 10:
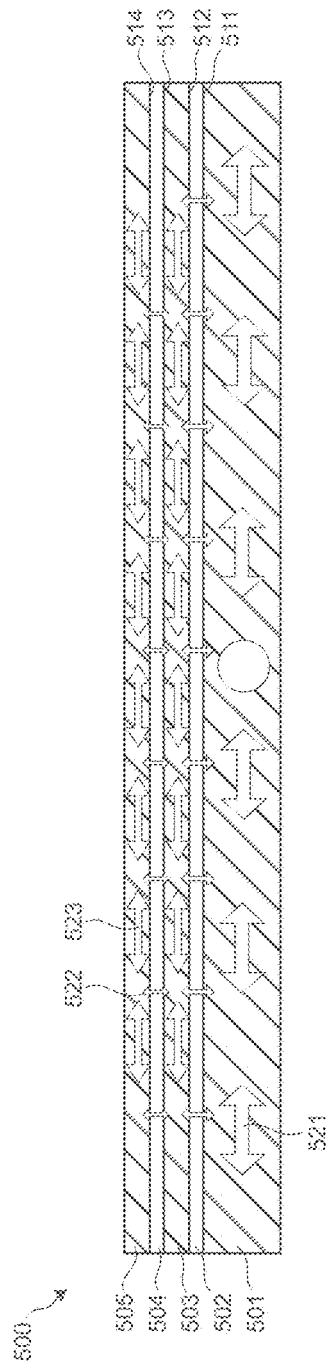
FIG. 10 is a schematic diagram illustrating heat flow in a diffusion-bonded block.

FIG. 9 illustrates the heat flow in a solid copper block and FIG. 10 illustrates heat flow in a diffusion-bonded block. In the solid copper block 400 illustrated in FIG. 9, heat may flow as freely in any direction as in any other direction, within the solid copper block. For example, heat will flow as freely in the vertical direction (as indicated by arrows 401) as in the lateral direction (as indicated by the arrows 402). Heat may also flow freely in any other direction within the copper block.

On the other hand, in the example of a diffusion-bonded block 500 shown in FIG. 10, heat flows laterally within copper layer 501, copper layer 503 and copper layer 505 much more readily than it does within the stainless steel layer 502 or stainless steel layer 504, or across the boundary 511 between copper layer 501 and stainless steel layer 502, boundary 512 between stainless steel layer 502 and copper layer 503, boundary 513 between copper layer 503 and stainless steel layer 504 or boundary 514 between stainless steel layer 504 and copper layer 505. The greater flow laterally within the copper layers is illustrated in FIG. 10 by the relative size of arrows 521 in copper layer 501 and arrows 523 in copper layer 503 and in copper layer 505, compared to the vertical arrows 522 in diffusion-bonded block 500.

Because heat flow in the vertical direction is inhibited, the structure of a diffusion-bonded block as shown in the example of FIG. 10 serves to inhibit thermal noise generated by outside sources from reaching and mixing with the thermal signal that is generated by the differential calorimeter. This occurs, in part, because thermal noise that is generated by sources external to the calorimeter may have a higher frequency than the actual differential calorimeter signal that is being detected. This thermal noise may, for example, enter the diffusion-bonded block from the top, the bottom or the side of the diffusion-bonded block. In those instances, the diffusion-bonded block may act as a low-pass filter, inhibiting the flow of heat from higher frequency sources, and thus reducing the noise in the thermal signal at the detectors.

As described below with reference to FIG. 17, the use of the diffusion-bonded block improves the calorimeter performance by reducing the noise level, by allowing the calorimeter to reach equilibrium much sooner and by reducing any temperature deviation between cells.

Figure 11:
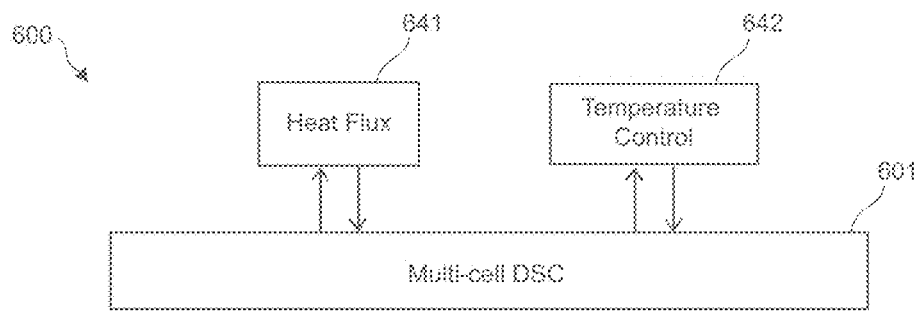
FIG. 11 is a schematic block diagram showing the main subsystems of an embodiment of a multi-cell DSC system.
Figure 12:
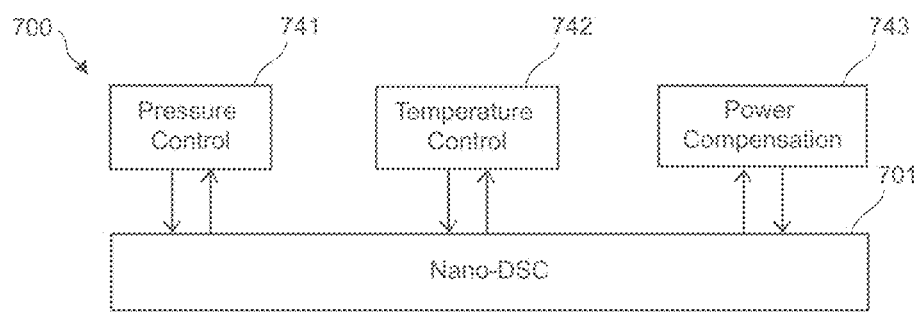
FIG. 12 is a schematic block diagram showing the main subsystems of an embodiment of a nano-DSC system.
Figure 13:
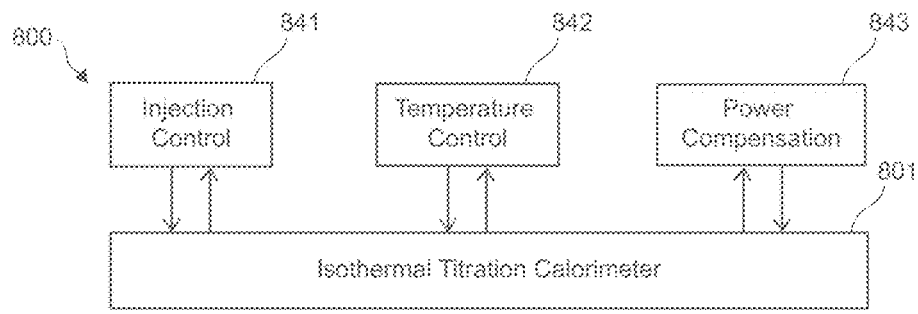
FIG. 13 is a schematic block diagram showing the main subsystems of an embodiment of an isothermal titration calorimeter.

Diffusion-bonded blocks may be used in a wide range of calorimeters or other instruments in which heat flow signals may be measured. For example, diffusion-bonded blocks may be used in a multi-cell DSC system, a nano-DSC system and an isothermal calorimeter system. FIG. 11, FIG. 12 and FIG. 13 are schematic block diagrams of an exemplary multi-cell DSC system, an exemplary nano-DSC system and an exemplary isothermal titration calorimeter system, respectively, shown with their control and sensing components. Thus FIG. 11 is a block diagram of multi-cell DSC system 600, which has two main subsystems, heat flux subsystem 641 and temperature control subsystem 642 in communication with a multi-cell DSC 601. FIG. 12 is a block diagram of a nano-DSC system 700 which has three main subsystems, pressure control subsystem 741, temperature control subsystem 742 and power compensation subsystem 743 in communication with nano-DSC 701. FIG. 13 is a block diagram of an isothermal titration calorimeter system 800, which has three subsystems, injection control subsystem 841, temperature control subsystem 842 and power compensation subsystem 843 in communication with isothermal titration calorimeter 801. These three calorimeter systems are described in greater detail below with reference to FIGS. 14-16.

Figure 14:
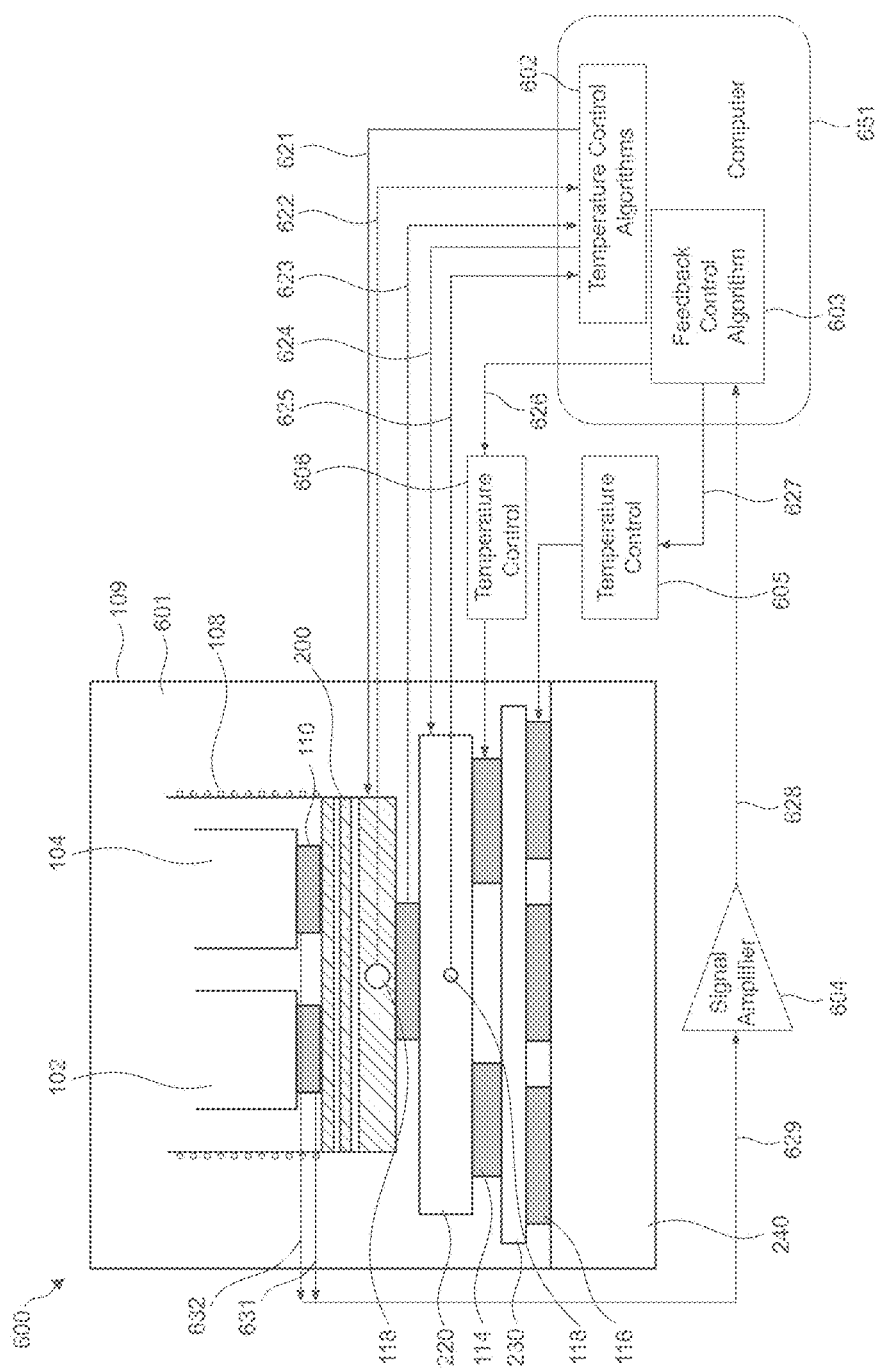
FIG. 14 is a schematic diagram of an embodiment of a multi-cell differential scanning calorimeter system.

The MCDSC calorimeter system shown in FIG. 14 includes an MCDSC 601 such as the MCDSC shown schematically in FIG. 1A, which shows reference cell 102, sample cell 104, heated jacket 108, diffusion-bonded block 200, block 220, block 230 and water bath 240, all within enclosure 109. FIG. 14 also shows following TEDs 114 and 116, and TED 110, which are all described above with reference to FIG. 1A. The temperature of diffusion-bonded block 200 and/or block 220 may be measured using temperature probes 118 such as RTDs, for example, or using thermocouples or other temperature sensors.

In the embodiment of an MCDSC system shown in FIG. 14, MCDSC system 600 has a heat flux subsystem 641 and a temperature control subsystem 642, as described above with reference to FIG. 11. In this embodiment, computer 651 may be used to control MCDSC 601, to collect data from its temperature sensors, and to calculate the differential heat flows to the samples with respect to the reference. In the temperature control subsystem 642, computer 651 controls MCDSC 601 using temperature control algorithm 602, feedback control algorithm 603, temperature control 605, and temperature control 606 via electrical connection 627, electrical connection 626, electrical connection 624 and electrical connection 621. The temperatures of the sample cell(s) and of the reference cell are monitored by TEDs 110 and provided to signal amplifier 604 via electrical connections 629, 631 and 632. The amplified signal from signal amplifier 604 is provided to feedback control algorithm 603 via electrical connection 628. In the heat flux subsystem 641, computer 651 collects the temperature data received from temperature sensors 118 via electrical connection 625, electrical connection 623 and electrical connection 622. Computer 651 then calculates the differential heat flow to or from each sample cell with respect to the reference based upon the signal received from each of the TEDs 110, as amplified by signal amplifier 604.

The MCDSC system shown in FIG. 14 maybe used, for example, to measure the rate of an endothermic or exothermic reaction by continuously scanning the temperature of the samples and reference over the temperature range of interest and measuring the heat flow to and/or from the sample cells with respect to the reference cell. Reaction rates may be measured isothermally by measuring the heat flow at a constant temperature, and observing the decreasing rate of the reaction until completion. The shelf life of certain materials may be determined by step-scanning the sample cells and reference cells at a series of isothermal steps to measure the steady-state heat rate at each of the isothermal temperatures and thus determine the activation energies and temperatures for transitions or reactions in these materials.

Figure 15:
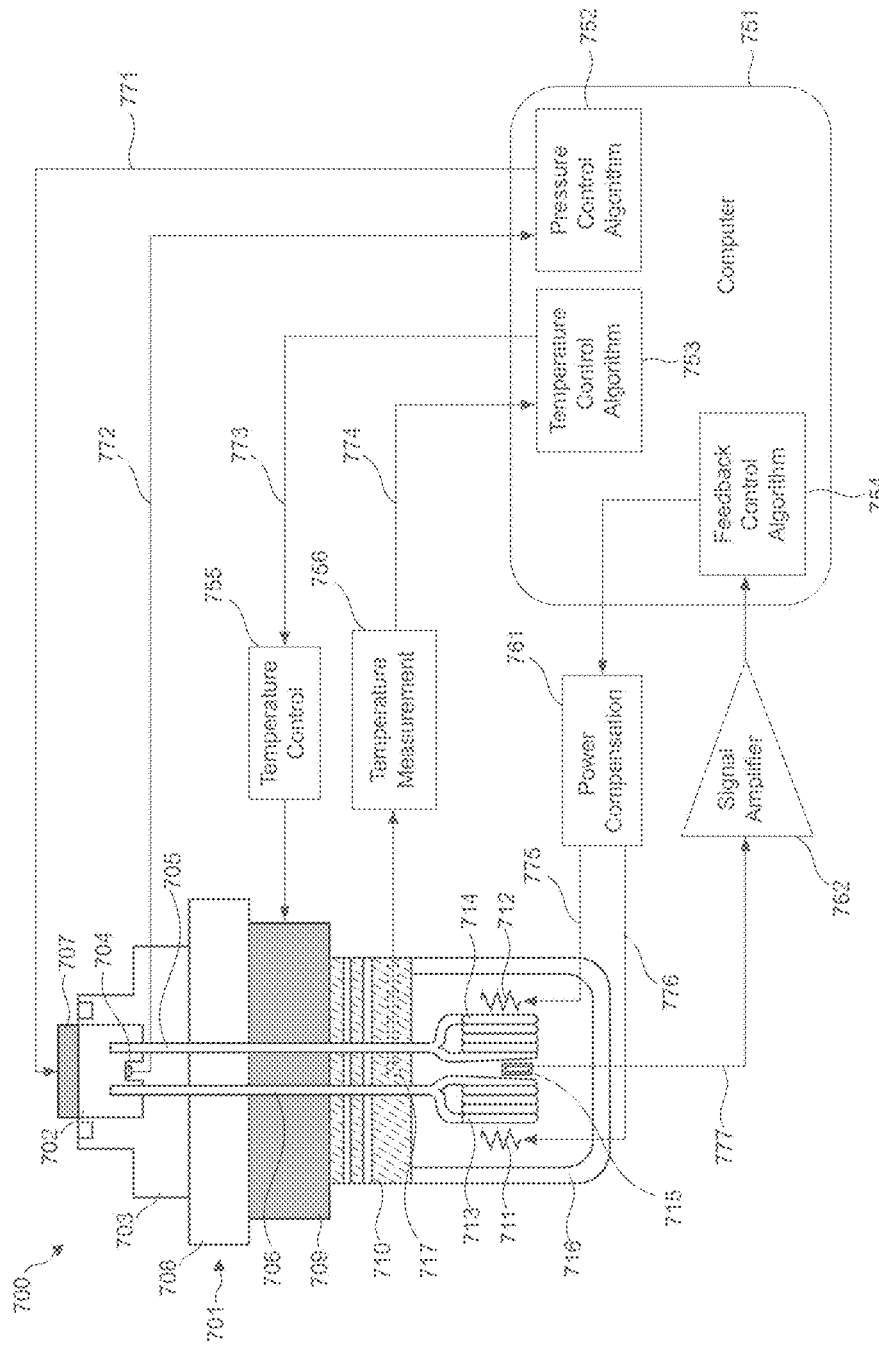
FIG. 15 is a schematic diagram of an embodiment of a nano-differential scanning calorimeter system.

FIG. 15 is a schematic diagram of a nano-DSC system 700. In this embodiment, nano-DSC system 700 uses power compensation to measure the differential heat flow to/from sample cell 714 compared to the heat flow to/from reference cell 713. In other embodiments, the nano-DSC may be a heat flux DSC. As described above with reference to FIG. 12, in this power compensation embodiment, the nano-DSC system has three main subsystems in communication with nano-DSC 701: a pressure control subsystem 741, a temperature control subsystem 742 and a power compensation subsystem 743.

As shown in FIG. 15, pressure control subsystem 741 (identified in FIG. 12) applies pressure to head space 702 directly above sample access tube 705 and reference access tube 706 using piston 707. Piston 707 is driven by a stepper motor (not shown) under the control of pressure control algorithm 752 via electrical connection 771. These components are held in position by metallic block 703, which could be, for example, a Hastelloy™ block and top plate 708. The pressure in head space 702 is measured by pressure transducer 704 and communicated to pressure control algorithm 752 via electrical connection 772. Pressure applied by piston 707 to head space 702 controls the pressure in sample access tube 705 and reference access tube 706, and thus the pressure applied to sample cell 714 and reference cell 713.

Temperature control subsystem 742 measures and controls the temperature of diffusion-bonded block 710 using temperature control module 755 and temperature measurement module 756 via electrical connections 773 and 774, respectively. Typically, the temperature of diffusion-bonded block 710 is measured by a temperature sensor, such as RTD temperature sensor 717 shown in FIG. 15. However, other temperature sensors may be used instead or an RTD sensor. The temperature of diffusion-bonded block 710 may be controlled by heating and cooling TED 709 under the control of temperature control module 755. TED 709 is positioned between top plate 708 and diffusion-bonded block 710. Temperature measurement module 756 measures the instantaneous temperature of diffusion-bonded block 710 and provides that temperature to temperature control algorithm 753. The computer system then drives the actual temperature to the desired temperature using, for example, a PID feedback loop to determine the output voltage that may be used to drive TED 709. A passive thermal shield 716, which is thermally connected to diffusion-bonded block 710, surrounds the sample cell 714 and the reference cell 713 isolating them from any temperature fluctuations.

The power compensation subsystem 743 includes sample cell 714 and reference cell 713, sample power compensation heater 712 and reference power compensation heater 711 and TED 715 that may be used to measure the instantaneous temperature difference between sample cell 714 and reference cell 713. The signal from TED 715 is provided to signal amplifier 762 via electrical connection 777 and then the amplified signal is provided as the input to feedback control algorithm 754 in computer 751, as shown in FIG. 15. Computer 751, feedback control algorithm 754 and power compensation module 761 then drive the temperature difference between sample cell 714 and reference cell 713 to zero, by adjusting the power provided to sample heater 712 and to reference heater 711 via electrical connection 775 and electrical connection 776. The sum of the power applied to the sample heater 712 and to the reference heater 711 is kept constant.

The nano-DSC system shown in FIG. 15 may be used, for example, to characterize the specific binding of a ligand (such as a drug to a receptor binding site) or to characterize non-specific binding (such as detergents binding to hydrophobic patches on a protein surface). It is particularly useful for characterizing very tight or slow binding interactions.

Figure 16:
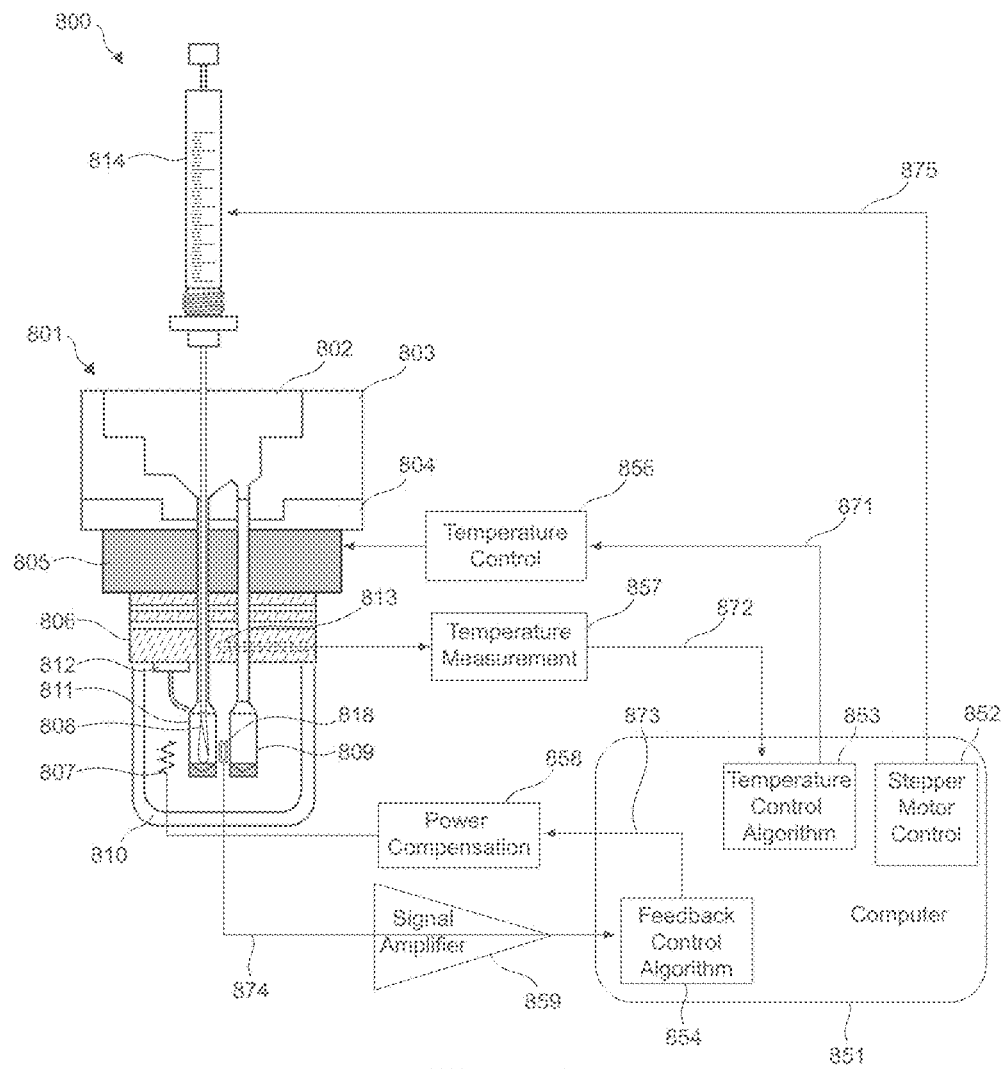
FIG. 16 is a schematic diagram of an embodiment of an isothermal titration calorimeter system.

FIG. 16 is a schematic diagram of an ITC system 800. In this embodiment, ITC system 800 uses power compensation to measure the differential heat flow to/from sample cell 811 compared to the heat flow to/from reference cell 809 in ITC 801. In other embodiments, the ITC system may measure the differential heat flux to/from the sample cell with respect to the reference cell. As described above with reference to FIG. 13, in this power compensation embodiment, the ITC system has three main subsystems in communication with ITC 801: an injection control subsystem 841, a temperature control subsystem 842 and a power compensation subsystem 843, as described below with reference to FIG. 16.

Injection control subsystem 841 includes syringe 814 that may be used to inject aliquots of a sample of a titrant (such as a ligand) into the sample cell 811 containing an analyte. The needle of syringe 814 passes through head space 802, polymer block 803, metallic block 804, heating and cooling TED 805 and diffusion-bonded block 806, and then enters sample cell 811. Polymer block 803 may be, for example, a PEEK block or a nylon block. Metallic block 804 may be, for example, an aluminum block.

The injection is carried out under the control of a stepper motor control 852 in computer 851 via electrical connection 875. Paddle stirrer 808 at the end of the needle of syringe 814 may be used to stir the sample to ensure that the injected titrant mixes well with the analyte in the sample cell 811.

Temperature control subsystem 842 includes heating and cooling TED 805 which is controlled by temperature control algorithm 853 via temperature control module 856 and electrical connection 871. The temperature of diffusion-bonded block 806 is measured by temperature sensor 813 and temperature measurement module 857. The output of temperature measurement module 857 is provided via electrical connection 872 as an input to temperature control algorithm 853 in computer 851 so that temperature control algorithm 853 can control the temperature of diffusion-bonded block 806.

Power compensation subsystem 843 includes sample cell 811, reference cell 809, cooling TED 812 and sample heater 807, which are held within passive thermal shield 810. The temperature difference between sample cell 811 and reference cell 809 is measured by TED sensor 818. Sample cell 811 may be cooled by cooling TED 812 or heated by heater 807. The signal from TED sensor 818 is provided to signal amplifier 859 via electrical connection 874, and the amplified signal is provided as the input to feedback control algorithm 854. Feedback control algorithm 854 controls power compensation module 858 via electrical connection 873 to adjust the power to sample heater 807 so as to drive the temperature difference measured by TED sensor 818 to zero. The additional power needed to drive the temperature difference to zero is used as a measure of the differential heat flow to the sample with respect to the reference.

Figure 17:
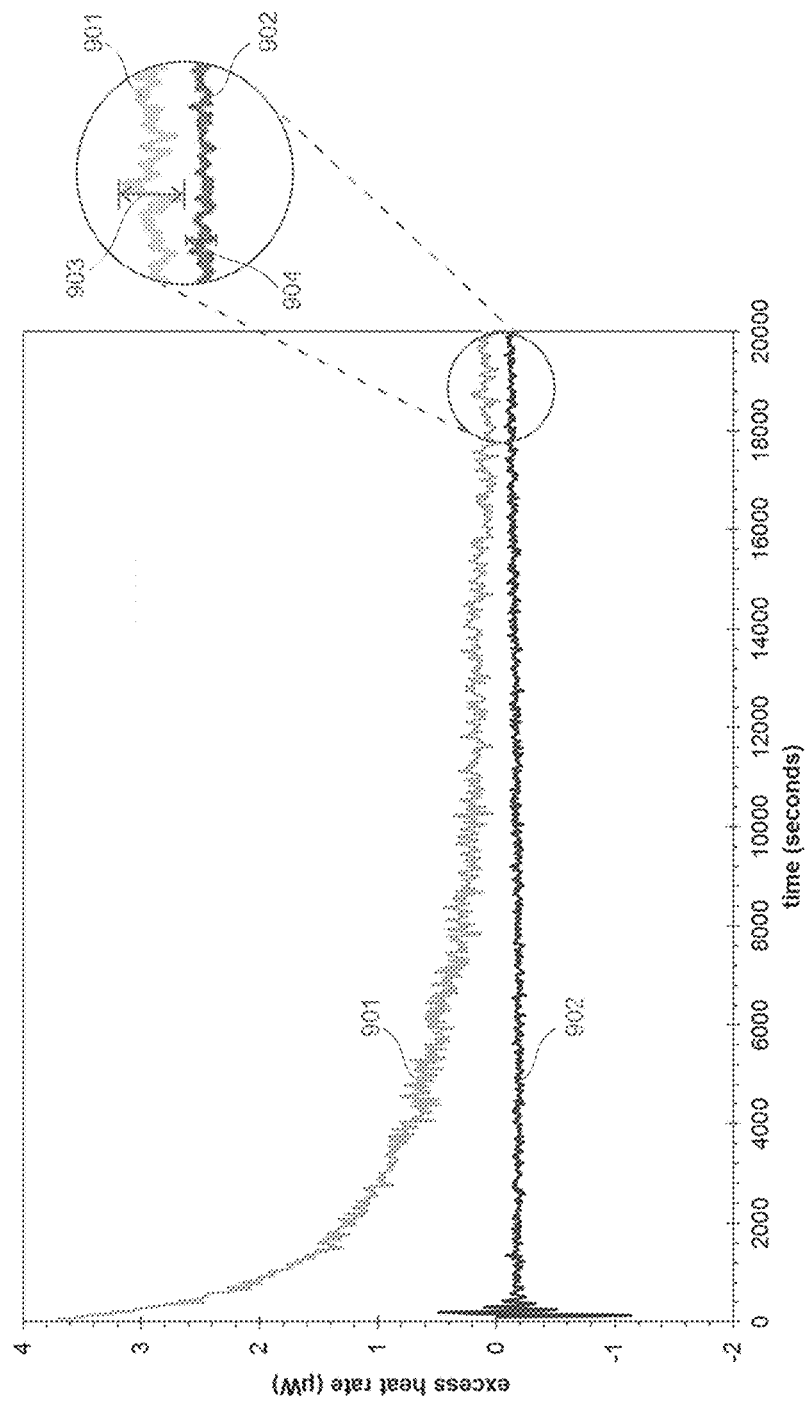
FIG. 17 is a comparison of the performance of a multi-cell DSC equipped with a multi-layer diffusion-bonded block to the performance of the multi-cell DSC equipped with a conventional block.

FIG. 17 a comparison of the performance of a representative example of a multi-cell DSC (such as the one shown schematically in FIG. 14) equipped with a multi-layer diffusion-bonded block to the performance of the same multi-cell DSC using a conventional block. The calorimeter signal shown as trace 901 is the signal produced by the representative example of a multi-cell DSC using a conventional block. The calorimeter signal shown as trace 902 is the signal produced by the representative example of a multiple-cell DSC using a diffusion-bonded block. As can be seen, the calorimeter using a conventional block does not reach equilibrium for at least 18000 seconds or about 5 hours, whereas the calorimeter using the diffusion-bonded block reaches equilibrium in about 800 seconds or about 13 minutes. As best shown in the blow-up in FIG. 17, the peak-to-peak noise level 903 of trace 901 after the calorimeter using a conventional block reaches equilibrium is roughly 2.5 times higher than the peak-to-peak noise level 904 of trace 902 after the calorimeter using a diffusion-bonded block reaches equilibrium. Also, although not evident from FIG. 17, the temperatures of the three sample cells in the multi-cell DSC using a diffusion-bonded block remain much more tightly clustered around their baseline equilibrium that do the sample cells in the multi-cell DSC that uses a conventional block.

Although the diffusion-bonded block has been described above as it may be used with a multi-cell differential scanning calorimeter, a nano-differential scanning calorimeter and an isothermal titration calorimeter, the diffusion-bonded block may also be used to provide improved calorimeter performance in other calorimeters by inhibiting any transmission of thermal noise generated outside the calorimeter to the thermal signal generated by the calorimeter, as well as improving the ability of the calorimeter to reach equilibrium. For example, the diffusion-bonded block may be used in a single sample cell differential scanning calorimeter, which would be similar to the multi-cell differential scanning calorimeter described above, but would have just one sample cell and just one reference cell (instead of having the three sample cells described above for the multi-cell differential-scanning calorimeter). Thus FIG. 1A and FIG. 14 would apply to a single sample cell calorimeter, with the understanding that the sample cell 104 illustrated in these figures is just one sample cell.

While various embodiments have been described, the description is intended to be exemplary, rather than limiting and it will be apparent to those of ordinary skill in the art that many more embodiments and implementations are possible that are within the scope of the embodiments. Accordingly, the embodiments are not to be restricted except in light of the attached claims and their equivalents. Also, various modifications and changes may be made within the scope of the attached claims.

What is claimed is:

1. A calorimeter comprising:
   a sample cell thermally coupled to a sample temperature sensor;
   a reference cell thermally coupled to a reference temperature sensor;
   a common heat sink thermally coupled to the sample cell and to the reference cell;
   wherein the common heat sink comprises a diffusion-bonded block, and
   wherein the diffusion-bonded block comprises a first metallic layer having a first thermal conductivity, a second metallic layer having a second thermal conductivity and a third metallic layer having a third thermal conductivity, wherein the second metallic layer is between the first metallic layer and the third metallic layer, and wherein the second thermal conductivity is different than the first thermal conductivity and the third thermal conductivity.

2. The calorimeter of claim 1, further comprising a fourth metallic layer having a fourth thermal conductivity and a fifth metallic layer having a fifth thermal conductivity.

3. The calorimeter of claim 2, wherein the first metallic layer is a copper layer, the second metallic layer is a stainless steel layer, the third metallic layer is a copper layer, the fourth metallic layer is a stainless steel layer and the fifth metallic layer is a copper layer.

4. The calorimeter of claim 2, wherein the first thermal conductivity, the third thermal conductivity and the fifth thermal conductivity are each at least about five times greater than the second thermal conductivity and the fourth thermal conductivity.

5. The calorimeter of claim 2, wherein the first metallic layer comprises a temperature sensor.

6. The calorimeter of claim 1, wherein the calorimeter is one of a differential scanning calorimeter, a multi-cell differential scanning calorimeter, a nano-differential scanning calorimeter and an isothermal titration calorimeter.

7. The calorimeter of claim 1, wherein the common heat sink is mounted on a scanning thermoelectric device.

8. The calorimeter of claim 1, further comprising a sample access tube and a reference access tube, and a pressure control system configured to apply pressure to the sample access tube and to the reference access tube.

9. The calorimeter of claim 1, further comprising a syringe configured to inject aliquots of a titrant into the sample cell.

10. A calorimeter system comprising:
    at least one sample cell and at least one reference cell in thermal communication with a common heat sink comprising a diffusion-bonded block, wherein the diffusion-bonded block comprises a first metallic layer having a first thermal conductivity, a second metallic layer having a second thermal conductivity and a third metallic layer having a third thermal conductivity, wherein the second metallic layer is between the first metallic layer and the third metallic layer, and wherein the second thermal conductivity is different than the first thermal conductivity and the third thermal conductivity;
    a temperature probe positioned to measure the temperature of the diffusion-bonded block; and
    a computer in electrical communication with the temperature probe and with either:
    a sample temperature sensor measuring a sample cell temperature and a reference temperature sensor measuring a reference cell temperature; or
    a differential temperature sensor measuring a differential temperature between the at least one sample cell and the reference cell;
    wherein the computer comprises a temperature control algorithm and a feedback control algorithm that control the temperature of the at least one sample cell and the temperature of the reference cell; and
    wherein the computer calculates the differential heat flow to the at least one sample cell with respect to the reference cell.

11. The calorimeter system of claim 10, wherein the diffusion-bonded block comprises at least five metallic layers, wherein the metallic layers alternately have a higher thermal conductivity and a lower thermal conductivity.

12. The calorimeter system of claim 11, wherein a first metallic layer of the diffusion-bonded block is a copper layer which is diffusion-bonded to a second metallic layer which is a stainless steel layer which is diffusion-bonded to a third metallic layer which is a copper layer which is diffusion-bonded to a fourth metallic layer which is a stainless steel layer which is diffusion-bonded to a fifth metallic layer which is a copper layer.

13. The calorimeter system of claim 10, wherein the calorimeter is one of a differential scanning calorimeter, a multi-cell differential scanning calorimeter, a nano-differential scanning calorimeter and an isothermal titration calorimeter.

14. The calorimeter system of claim 10, wherein the metallic layers have facing surfaces that have a surface roughness that is not greater than 8 micro-inches.

15. The calorimeter system of claim 10, wherein the top surface of the top layer of the diffusion-bonded block is parallel to the bottom surface of the diffusion-bonded block to within 0.002 inches.

16. A calorimeter comprising:
a sample cell and a reference cell; and
a common heat sink comprising a first diffusion-bonded block thermally coupled to the sample cell and to the reference cell;
wherein the first diffusion-bonded block comprises a first metallic layer diffusion-bonded to a second metallic layer, a third metallic layer diffusion-bonded to the second metallic layer and to a fourth metallic layer, and a fifth metallic layer diffusion-bonded to the fourth metallic layer;
wherein the first metallic layer, the third metallic layer and the fifth metallic layer are characterized by having higher thermal conductivities and the second metallic layer and the fourth metallic layer are characterized by having lower thermal conductivities; and
wherein the first metallic layer comprises a temperature probe.

17. The calorimeter of claim 16, wherein each of the first metallic layer, the second metallic layer, the third metallic layer, the fourth metallic layer and the fifth metallic layer are each characterized by each having thermal conductivities, and the thermal conductivities of the first metallic layer, the third metallic layer and the fifth metallic layer are each at least about five times greater than the thermal conductivities of each of the second metallic layer and the fourth metallic layer.

18. The calorimeter of claim 16, wherein the first metallic layer is a copper layer, the second metallic layer is a stainless steel layer, the third metallic layer is a copper layer, the fourth metallic layer is a stainless steel layer and the fifth metallic layer is a copper layer.

19. The calorimeter of claim 16, wherein the first metallic layer, the third metallic layer and the fifth metallic layer are each one of a gold layer, a silver layer and an aluminum layer.

20. The calorimeter of claim 16, further comprising a second diffusion-bonded block in thermal communication with the first diffusion-bonded block.

21. The calorimeter of claim 16, further comprising a sixth metallic layer diffusion-bonded to the fifth metallic layer and a seventh metallic layer diffusion-bonded to the sixth metallic layer, wherein the thermal conductivity of the sixth metallic layer is lower than the thermal conductivity of the seventh metallic layer.

* * * * *